United States Patent [19]  
Coupland et al.

[11] 4,164,473  
[45] Aug. 14, 1979

[54] ORGANO MOLYBDENUM FRICTION REDUCING ANTIWEAR ADDITIVES

[75] Inventors: Keith Coupland, Sarnia; Clinton R. Smith, Camlachie, both of Canada

[73] Assignee: Exxon Research & Engineering Co., Florham Park, N.J.

[21] Appl. No.: 928,817

[22] Filed: Jul. 28, 1978

Related U.S. Application Data

[63] Continuation of Ser. No. 843,963, Oct. 20, 1977, abandoned.

[51] Int. Cl.$^2$ .................. C10M 1/48; C10M 3/42; C07F 00/00; C10M 5/24
[52] U.S. Cl. .................. 252/32.7 E; 44/68; 252/42.7; 252/46.6; 260/429 R; 260/429 J
[58] Field of Search ............ 44/68; 260/429 R, 429 J; 252/32.7 E, 42.7, 46.6

[56] References Cited

U.S. PATENT DOCUMENTS

| 3,010,902 | 11/1961 | Spengler et al. .............. 252/46.4 |
| 3,184,410 | 5/1965 | Bretherick .................. 252/42.7 |
| 3,252,910 | 5/1966 | Oberright ................... 252/42.7 |
| 3,356,702 | 12/1967 | Farmer et al. ............... 252/42.7 |
| 3,931,242 | 1/1976 | Darvans et al. .............. 260/429 R |

FOREIGN PATENT DOCUMENTS

| 1060079 | 6/1959 | Fed. Rep. of Germany . |
| 1066309 | 10/1959 | Fed. Rep. of Germany . |
| 1075253 | 2/1960 | Fed. Rep. of Germany . |
| 1095973 | 12/1960 | Fed. Rep. of Germany . |
| 882295 | 11/1961 | United Kingdom . |

Primary Examiner—Delbert E. Gantz  
Assistant Examiner—I. Vaughn  
Attorney, Agent, or Firm—Roland A. Dexter

[57] ABSTRACT

Hydrocarbon-soluble organo molybdenum complexes obtained as the reaction product of a hydrocarbyl substituted hydroxy alkylated amine e.g. N,N',N'-tris(2-hydroxy ethyl)-n-tallow-1,3-diaminopropane, with about one molar equivalent of a molybdenum compound, e.g. ammonium molybdate, are useful hydrocarbon additives particularly in combination with an oil-soluble sulfur donor, e.g. a metal dialkyl dithiophosphate to provide an additive combination for lubricating oils since the lubricating compositions comprising these co-additives exhibit improved anti-friction and anti-wear properties.

9 Claims, No Drawings

ORGANO MOLYBDENUM FRICTION REDUCING ANTIWEAR ADDITIVES

This is a continuation of application Ser. No. 843,963, filed Oct. 20, 1977, now abandoned.

BACKGROUND OF THE INVENTION

The present invention relates to hydrocarbon-soluble molybdenum complexes of hydroxy amines, their method of preparation and their utility as an additive for hydrocarbon compositions such as gasoline, fuel oil and lubricating oils including greases, industrial oils, gear oils and lubricants for engines and other equipment having moving parts operating under boundary lubricating conditions.

There are many instances, as is well known, particularly under "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known additives which may be classified as antiwear, anti-friction and extreme pressure agents and some may in fact satisfy more than one of these functions as well as provide other useful functions, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates are one of the additives which are known to exhibit antioxidant and antiwear properties. The most commonly used additives of this class are the zinc dialkyl dithiophosphates which are conventionally used in lubricant compositions. While such zinc compounds afford excellent oxidation resistance and exhibit superior antiwear properties, it has heretofore been believed that the same increases or significantly limits the ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when anti-friction agents are included in the composition.

Known ways to solve the problem of energy losses due to high friction, e.g. in crankcase motor oils include the use of synthetic ester base oils which are expensive and the use of insoluble molybdenum sulfides which have the disadvantage of giving the oil composition a black or hazy appearance.

Other types of molybdenum compounds taught to be useful in lubricating oils include the alkyl esters of molybdic acid as corrosion inhibitors (see U.S. Pat. No. 2,805,997) and nitrogenous thiomolybdates as metal antiwear additives which are said to function by providing a coating of reduced coefficient of friction (see U.S. Pat. No. 2,938,869).

Similarly, antifriction agents or oiliness or lubricity agents, as the same are often referred to in the prior art, function by forming a coating on the surface of the moving metal parts. As in the case of antiwear agents, however, the coating bonds are, generally, effected physically, rather than chemically, and, indeed, the bonding between an antifriction agent and the surface is, generally, weaker than the bond formed between an antiwear agent and the metal surface.

In light of the foregoing, the need for improved lubricating compositions that will permit operation of moving parts under boundary conditions with reduced friction is believed to be readily apparent. Similarly, the need for such a composition that can include conventional base oils and other conventional additives and can be used without the loss of other desirable lubricant properties, particularly those provided by zinc dialkyl dithiophosphates, is also readily apparent.

SUMMARY OF THE INVENTION

It has now surprisingly been discovered that the foregoing and other disadvantages of the prior art lubricating additives and lubricating compositions formulated therewith can be overcome with a novel class of organo molybdenum complexes believed to be represented by the following formula I:

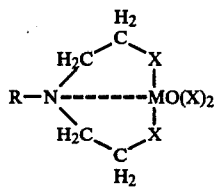

wherein R is a substantially hydrocarbyl group containing from 1 to 50, preferably 12 to 28, carbon atoms and X is selected from sulfur or oxygen. These complexes are particularly useful when used in combination with a sulfur donor, e.g. zinc dialkyl dithiophosphate. It is understood that the R substituent can contain substituted pendant hetero groups provided they do not detrimentally alter the hydrocarbon solubility of the molybdenum complex.

In accordance with the present invention, the foregoing and other objects and advantages are accomplished with a hydrocarbon composition comprising a major portion of a hydrocarbon e.g. a lubricating oil and at least a friction reducing amount of said hydrocarbon soluble molybdenum complex and preferably a lubricity enhancing combination of: (a) said hydrocarbon soluble molybdenum complex; and, (b) an oil-soluble sulfur donor, preferably zinc dialkyl dithiophosphate, and, if desired, at least a sludge-dispersing amount of an oil-soluble dispersant e.g. an ashless dispersant and at least a rust-inhibiting amount of a rust inhibitor. In practice, the lubricity enhancing combination is present in an amount sufficient to provide from about 0.005 to 0.2, preferably 0.03 to 0.15, optimally about 0.1, wt. % molybdenum and at least about 0.25, e.g. 0.25 to 1, wt. % sulfur donor, all weight percent being based on the total weight of the oil composition.

DETAILED DESCRIPTION OF THE INVENTION

OIL-SOLUBLE ORGANO MOLYBDENUM COMPOUND

As earlier described, the hydrocarbon-soluble molybdenum complexes of the invention are believed to conform to said Formula I. The R group of said Formula I as defined is substantially hydrocarbyl and thus is alkyl, aryl, aralkyl, cycloalkyl, or alkaryl; however, the hydrocarbyl group may contain polar substituents such as amino, aminoalkyl, hydroxy, hydroxyalkyl, halo, mercapto, keto, phosphinyl, phosphoryl, thiophosphoryl and dithiophosphoryl radicals.

Specific examples of the R group includes methyl, ethyl, propyl, isopropyl, isobutyl, n-butyl, sec-butyl, terbutyl, n-hexyl, heptyl, octyl, decyl, dodecyl, tridecyl, heptadecyl, octadecyl, phenyl, butyl phenyl, dibutyl phenyl, octyl phenyl, nonyl phenyl, dodecyl phenyl, polyisobutyl substituted phenyl, polypropylene substituted phenyl, chlorophenyl and naphthyl; particularly useful R groups are alkyl amino alkyl substituents selected from the class defined by the formula:

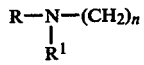

wherein R is substantially hydrocarbyl as previously defined preferably alkyl, R' is hydrogen or R and n is an integer from 2-30, preferably 2-6 and optimally 2-3.

The organic molybdenum complexes are the reaction product of a tertiary amine having hydroxy or thiol functionality and a source of molybdenum. The aforesaid tertiary amines can be characterised by Formula II:

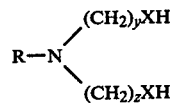

wherein R and X are each the same as previously described and y and z are integers ranging from 1 to 3, preferably about 2. These tertiary amines having hydroxy functionality are readily produced from the reaction of alkylene oxides, e.g. ethylene oxide and a substantially hydrocarbyl substituted monoamine, preferably a fatty alkyl monoamine such as tallow amine and oleylamine. The tertiary amines having thiol functionality are similarly readily produced from the reaction of alkylene episulfide and said substantially hydrocarbyl substituted monoamine. These fatty alkylamines are usually derived from naturally occurring fatty acids and may be coco-amine, soyaamine, tallow amine, rape amine and their fully hydrogenated derivatives. These amines derived from natural fats are mixtures of hydrocarbyl amines with hydrocarbyl groups ranging from eight to twenty-four carbons.

A particularly useful reactant for the preparation of the molybdenum complex can be characterized by Formula III:

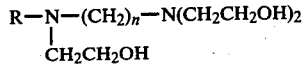

wherein R is same as previously defined and n is an integer from 2-30, preferably 2-6 and optimally 3. These reactants are readily produced by the cyanoethylation of fatty amines followed by reduction and hydroxyalkylation with an alkylene oxide such as ethylene oxide.

Particularly useful compounds are: bis(2-hydroxyethyl) alkyl amines e.g. bis(2-hydroxyethyl) cocoamine prepared by the reaction of a tertiary amine having a $C_{12}$ to $C_{18}$ alkyl group and ethylene oxide; and, N,N',N'-tris(2-hydroxyethyl)-N-alkyl-1,3-diaminopropane e.g. N,N',N'-tris (2-hydroxyethyl)-N-tallow-1,3-diaminopropane prepared by the reaction of an N-alkyl trimethylene diamine and ethylene oxide. These particularly useful compounds are commercially available as Ethomeen ® Polyethoxylated Amines and Ethoduomeen ®, Polyethoxylated Diamines, respectively, from the Armak Corporation of Chicago, Ill.

The source of molybdenum is a molybdenum oxygen or sulfur-containing compound capable of reacting with the tertiary amine to provide a molybdenum complex containing from about 0.5 to 20, preferably 2 to 10, optimally about 7, wt.% molybdenum based on the total weight of said ester. The sources of molybdenum include molybdic trioxide also known as molybdic anhydride, ammonium thiomolybdate, ammonium bismolybdate, molybdenum halides, and ammonium heptamolybdate tetrahydrate, with the latter being preferred.

The organo molybdenum complex is substantially an equimolar i.e. from about 1 to 1.2 moles/mole product of the tertiary amine and molybdenum source, respectively. The reaction is readily carried out as a typical esterification reaction with heat provided to accelerate said reaction as well as to remove the water of esterification. The reaction can be carried out in an inert solvent such as toluene or light hydrocarbon oil or without a solvent. The esterification can therefore be conducted at from about 80° C. to 150° C. for a period of from about 1 to 40 hours and/or at least until the stoichiometric amount of water of esterification is removed, as by nitrogen sparging or distillation at atmospheric or reduced pressure.

SULFUR DONORS

It has been discovered that the novel class of hydrocarbon-soluble organo molybdenum complexes provide suitable lubricity improvement in lubricating oils when used in combination with an active sulfur donor which can be defined as a compound which when used in admixture with said molybdenum complex reduces the coefficient of friction at least about 10%. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following formula:

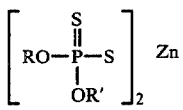

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl, n-hexyl, i-hexyl, n-heptyl, n-octyl, decyl, dodecyl, octadecyl, 2-ethylhexyl, phenyl, butylphenyl, cyclohexyl, methylcyclopentyl, propenyl, butenyl etc. In order to obtain oil solubility, the total number of carbon atoms in the dithiophosphoric acid will average about 5 or greater.

The zinc dihydrocarbyl dithiophosphates which are useful as the coadditive, i.e. sulfur donor of the present invention, may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is realized.

As noted earlier an equally suitable active sulfur donor is the dihydrocarbyl esters of dithiophosphoric acid which may be represented by the formula

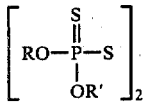

where R and R' are as previously defined. Particularly useful is the dibutylphenyl dithiophosphate.

The phosphosulfurized terpenes as represented by pinene, dipentene, allo-ocimene, etc., are another group of dithiophosphate diesters which are active sulfur donors. Of the terepenes, the bicyclic pinene is preferred. The phosphosulfurized terpane is readily obtained by reaction of about one mole of diester of thiophosphoric acid and one mole of pinene at a temperature of at least 100° C. e.g., 100° C. to 200° C. The preferred active sulfur donor can be characterized as the bornyl ester of dihydrocarbyl ($C_2$-$C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, naphthalene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmitolic, behenic, stearic, palmitic, lauric, capric, etc. as well as mixtures obtained from vegetable and animal oils such as tall oil.

The sulfurized alkyl phenols are generally $C_4$ to $C_{20}$ alkyl phenol sulfide dithiophosphoric acids having the general formula

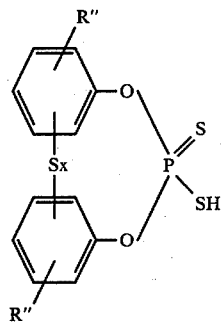

wherein R" represents a $C_4$-$C_{20}$ alkyl substituent and x is an integer in the range of 1 to 3 and is shown by t-octyl phenol dithiophosphoric acid. These sulfurized alkyl phenols are readily produced by sulfurizing an alkyl phenol with a sulfur halide and then reacting the phenol sulfide with a sulfide of phosphorous, e.g. $P_2S_5$.

Other Additives For Lubricating Compositions

In addition to the organo molybdenum complex and active sulfur donor the lubricating oil composition may contain other well known lubricating oil additives to provide trouble free operation of the lubricated equipment, such as ashless dispersants, metallic detergents, supplemental oxidation and corrosion inhibitors, extreme pressure agents, rust inhibitors, pour point depressants, viscosity index improvers, etc.

1. Ashless Dispersants

As used herein, the terminology "ashless dispersant" is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

$$NH_2(CH_2)_n-[NH(CH_2)_n]_m-NH_2$$

wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di(2-aminoethyl) ethylenediamine may also be used. Other aliphatic polyamino compounds that may be used are N-aminoalkylpiperazines, e.g. N-(2-aminoethyl) piperazine. Mixtures of alkylene polyamines approximating tetraethylene pentamine are commercially available, e.g. Dow E-100 sold by Dow Chemical Company of Midland, Mich.

Representative dispersants are formed by reacting about one molar amount of polyisobutenyl succinic anhydride with from about one to about two molar amounts of tetraethylene pentamine or with from about 0.5 to 1 moles of a polyol, e.g. pentaerythritol.

It is possible to modify the ashless dispersants generally by the addition of metals such as boron in order to enhance the dispersancy of the additive. This is readily accomplished by adding boric oxide to the reaction mixture after the imidation or esterification is substantially complete and heating the mixture at temperatures of 100° to 150° C. for a few hours.

2. Other Additives

Detergents useful in conjunction with dispersants, preferably the ashless type, include normal, basic or overbased metal, e.g. calcium, magnesium, etc. salts of petroleum naphthenic acids, petroleum sulphonic acids, alkyl benzene sulphonic acids, oil soluble fatty acids, alkyl salicylic acids, alkyl phenols, alkylene-bis-phenols, and hydrolyzed phosphosulphurized polyolefins.

Oxidation inhibitors include phenols, amines, sulphurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate, post grafted polymers of ethylene propylene with an active monomer such as maleic anhydride which may be further reacted with an alcohol or an alkylene polyamine, styrene/maleic anhydride polymers post reacted with alcohols and amines, etc.

The hydrocarbons in which the additive combination of the invention is most effective are mineral oils having a viscosity as measured by ASTM D-445 of from about 2 to 40, preferably 5 to 20 centistokes at 99° C.

If the additive combination of oil-soluble organo molybdenum complex and active sulfur donor are used as an additive concentrate, the concentrate may consist essentially of from about 5 to 80% of the additive combination, the remainder being a satisfactory solvent such as kerosene, mineral oil, a naphtha and the like. The preferred concentrate contains about 10 to 60% of the additive combination in the solvent.

Whether the organo molybdenum complex is used alone or in combination with an active sulfur donor, its concentration may vary appreciably with the particular hydrocarbon. For example, when said molybdenum complex is used alone in a fuel such as gasoline, the concentration of the complex ranges from 10 to 1,000, preferably 20 to 50 weight parts per million based on the total weight of the fuel composition, whereas as a lubricant, it is used in combination with the active sulfur donor, which combination ranges from about 0.5 to 5, preferably 1 to 3 wt. % based on the total weight of the lubricating oil.

The invention will be further understood by reference to the following examples which illustrate a preferred form of the invention and compares the same with different, though similar compositions.

The following examples illustrate more clearly the compositions of the present invention. However, these illustrations are not to be interpreted as specific limitations on this invention.

EXAMPLE 1

Ethoduomeen T-13, a commercially available ethoxylated amine from Armak Corporation, Chicago, Ill., approximating in structure to N,N$^1$-tris(2 hydroxyethyl)-N-tallow-1,3-diaminopropane, (20.8 g), toluene (20.8 g) and molybdic oxide (5.23 g) were refluxed together with stirring. Water released in the reaction was collected by means of a Dean and Stark receiver until a total of 0.65 cm$^3$ had been isolated. The organo molybdenum complex reaction product was diluted with light mineral oil (25 g) filtered and stripped of volatiles. The final product containing about 50 wt. % of said complex product was a viscous amber liquid which analyzed for 3.77 wt. % molybdenum.

EXAMPLE 2

Ethoduomeen T-13 (36 g), toluene (14 g) and ammonium molybdate (11.3 g) were refluxed together removing water continuously. Reaction was continued until 2.3 cm$^3$ had been collected. The product was then diluted with light mineral oil (45 g), filtered and stripped free of toluene. The product was a dark red viscous oil containing about 50 wt. % complex product.

EXAMPLE 3

Ethoduomeen T-13 (330.6 g), toluene (100 cm$^3$), ammonium molybdate (103.8 g) and 1 drop of silicone antifoam were reacted as in Example 2. Water (23 cm$^3$) was removed as the toluene-water azeotrope. The product was filtered and stripped to yield a dark red viscous liquid.

EXAMPLE 4

Ethomeen C/12, a commercially available ethoxylated amine from said Armak Corporation, approximating in structure to N,N-bis (2-hydroxyethyl)tridecylamine (30 g), toluene (10 g), ammonium molybdate (17.6 g) and antifoam 1 drop were refluxed together removing water continuously. Water (3.2 cm$^3$) was removed, the product was diluted with (30 g) and filtered to yield a brick red waxy solid.

EXAMPLE 5

Ethoduomeen T-13 (20.41 kg) light mineral oil (24.49 kg) and ammonium heptamolybdate tetrahydrate (6.4 kg) were stirred together with heating at 150° C. for 20 hrs. Water and ammonia were allowed to be distilled from the reaction. During the last 4 hrs. a nitrogen sparge was applied to remove the last traces of volatile material. At the end of the reaction period there was isolated a dark red viscous oil containing about 50 wt. % complex product and 7.0% molybdenum.

EXAMPLE 6

Three lubricating oil compositions were prepared by blending together the individual components, noted below, usually at a slightly elevated temperature, i.e. from about 45° C. to above 65° C. to insure complete mixing. The final compositions of Blends 6A, 6B and 6C formulated into 3 10W30 SE quality automotive engine oils were as follows:

|  | Blends wt. % Active Ingredient | | |
|---|---|---|---|
|  | 6A | 6B | 6C |
| Mineral Oil | 94.9 | 93.9 | 90.8 |
| Ashless Dispersant | 2.9 | 3.4 | 4.1 |
| Magnesium Sulphonate | 0.2 | 0.3 | — |
| ZDDP[1] | 0.9 | 0.7 | 1.8 |
| Rust-Inhibitor | 0.1 | — | 0.1 |
| Viscosity Index Improvers | 1.0 | 1.0 | 1.1 |
| Silicone Defoamer | 0.01 | 0.01 | 0.01 |
| Ashless Antioxidant | — | 0.7 | — |
| Metal Detergent-Inhibitor | — | — | 2.1 |

[1]Zinc dihydrocarbyl dithiophosphate such as zinc dinonyl phenol dithiophosphate.

These formulated blends were themselves and in modified form according to the teachings of this invention subjected to several testing procedures as hereinafter set forth:

1. Testing Procedure A

This procedure measures the coefficient of friction between a journal and a 120° section of a journal bearing when lubricated by the test fluid lubricant. A journal (1.5" outer diameter) is fitted on a shaft supported by two antifriction bearings. The bearing section is loaded against the journal by a load lever and a series of knife edges connected each to an arm. A bearing block, which holds the bearing section against the journal, is self-aligning thus eliminating any problem of edge loading. The frictional force between the bearing section and the journal is measured by a friction lever.

The shaft is coupled to a variable speed transmission which allows surface speeds of the journal to be varied from 0.3 to 1.6 cm/sec. Bearing loads can be increased from 0 to 3000 psi by adding weights to the pan supported by the load lever. Infra-red lamps keep the mass of the bearing at the desired test temperature (ambient to 130° C.) as measured by a thermocouple in a thermowell.

The test lubricant is placed in a shallow pan and held such that the bottom face of the journal touches the oil. The tester and test lubricant are brought to 110° C. With only the weight hanger on the load lever the machine is started at 80 rpm. 36.6 kg of weights are added to the pan giving an effective contact pressure of 2600 psi. Sufficient weight is placed on the load lever to overcome the friction force and keep it in the down position. The following speed cycle is carried out allowing five minutes of operation at each speed to allow lubrication conditions to stabilize. A torque measurement is made at speed.

| Speeds (rpm) | 80, | 60, | 30, | 20, | 10, | 7, | 3, | 1.5 |
|---|---|---|---|---|---|---|---|---|
| (cm/sec) | 16, | 12, | 6, | 4, | 2, | 1.4, | 0.6, | 0.3 |

The tester is then operated at constant speed, 30 rpm, for a 3-hour period. The speed cycle is repeated. If required, the tester can be operated at constant speed, 30 rpm, overnight (~17 hours) and the speed cycle repeated.

Between test lubricants, the tester is flushed with base case oil and run in the base case oil until its previous performance is repeated, taking the tester apart and cleaning it if necessary.

2. Testing Procedure B

The Roxana Four-ball wear tester with the Brown/GE modification from Roxana Machine Works, St. Louis, MO was used to measure friction properties by the following procedure. The tester was assembled in the normal wear procedure as described in ASTM D2266-67 using four ½" bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test is carried on until frictional force has stabilized. The test at 25 rpm is carried out at 100° C. and 15 kg for 15 minutes or until frictional force has stabilized.

3. Testing Procedure C

This is a fuel economy test as detailed in the Federal Register 37 #221 24316 (1972), ibia 41 #100 21002 (1976). This test was conducted using a full size test automobile equipped with a 350 CID 8 cylinder engine. Fuel consumption was measured in both the FTP and HWFET test cycles and the combined FTP/HWFET) fuel consumption determined.

4. Testing Procedure D

This measured the fuel consumption of a full size test automobile equipped with a 350 CID 8 cylinder engine. The test involves placing the vehicle on a Clayton chassis whereby the vehicle can operate under controlled simulated driving conditions. This is achieved by variation in loading of the rollers driven by the rear wheels of the vehicle. The rear tires were inflated to 49 psi and cooled by fans to avoid overheating. Engine cooling was obtained by a fan driving air over the radiator. The car was operated at conditions simulating driving along a level highway at the two speeds of 30 and 55 mph. Loading was based on the EPA test as laid down in the Federal Register as referenced in testing procedure C. When the vehicle was fully warmed up, fuel consumption was determined in triplicate. The data were then averaged to give the measured fuel consumption at the particlar test condition.

The compounds of the invention were then evaluated by subjecting the product of Example 5 to a study of its utility as a lubricity enhancing and/or antiwear additive for lubricating oils by using the Testing Procedures A-D. The weight percentage of amounts of molybdenum complex added is given in amount of complex added.

The results of tests under Procedure A are set forth in Table I.

The results of tests under Procedure B are set forth in Table II.

The results of tests under Procedure C are set forth in Table III.

The results of tests using Procedure D are set forth in Table IV.

TABLE I

| Test | Lubricant | Added Molybdenum Complex wt. % | Coefficient of Friction 16cm/sec | Coefficient of Friction 0.3cm/sec. | % Friction Reduction 16 cm/sec. | % Friction Reduction 0.3cm/sec. |
|---|---|---|---|---|---|---|
| 1 | A | — | 0.120 | 0.141 | — | — |
| 2 | A | 0.5 | 0.061 | 0.090 | 49.2 | 36.2 |
| 3 | A | 1.0 | 0.022 | 0.069 | 81.7 | 50.0 |

TABLE II

| Test | Lubricant | Added Molybdenum Complex wt. % | Coefficient of Friction 46 cm/sec. | Coefficient of Friction 1 cm/sec. | % Friction Reduction 46 cm/sec. | % Friction Reduction 1 cm/sec |
|---|---|---|---|---|---|---|
| 4 | A | — | 0.084 | 0.115 | — | — |
| 5 | A | 0.5 | 0.049 | 0.101 | 41.7 | 12.2 |
| 6 | A | 1.0 | 0.040 | 0.074 | 52.4 | 35.7 |
| 7 | A | 1.5 | 0.039 | 0.077 | 53.6 | 33.0 |
| 8 | C | — | 0.093 | 0.119 | — | — |
| 9 | C | 0.5 | 0.037 | 0.041 | 60.2 | 65.5 |
| 10 | A* | 1.5 | 0.103 | 0.114 | (10.8) | 4.2 |

*Lubricant blend A was modified by formulation without the ZDDP.
It was also noted that the lubricant used in Test No. 10 resulted in a wear reduction of 57% of that resulting from Test No. 8

TABLE III

| Test | Lubricant | Added Molybdenum Complex Wt. % | FTP* | HWFET** | Combined |
|---|---|---|---|---|---|
| 11 | A | — | 13.37 | 18.69 | 15.40 |
| 12 | A | 1.0 | 14.04 | 19.07 | 15.93 |
| Thus 12 shows a percent improvement over 11 of | | | 4.2 | 2.0 | 3.4 |

*Federal Test Procedure
**Highway Fuel Economy Test

TABLE IV

| Test | Lubricant | Added Molybdenum Complex Wt.% | Fuel Consumption (mpg) 30 mph | Fuel Consumption (mpg) 55 mph | % Improvement 14 over 13 30 mph | % Improvement 14 over 13 55 mph |
|---|---|---|---|---|---|---|
| 13 | B | — | 17.10 | 21.33 | | |
| 14 | B | 1.0 | 18.27 | 21.90 | 6.8 | 2.7 |
| | | | | | 16 over 15 30 mph | 16 over 15 55mph |
| 15 | A | — | 16.53 | 20.93 | | |
| 16 | A | 1.0 | 17.78 | 21.72 | 7.6 | 3.8 |

From the foregoing, it is shown that the additives of the invention provide lubricity enhancement to lubricating oils when an active sulfur donor is present and that they have utility as antiwear additives for lubricating oils.

It is to be understood that the examples present in the foregoing specification are merely illustrative of this invention and are not intended to limit it in any manner; nor is the invention to be limited by any theory regarding its operability. The scope of the invention is to be determined by the appended claims.

What is claimed is:

1. An organo molybdenum complex represented by the formula

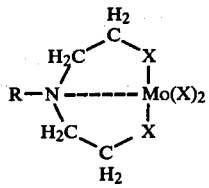

wherein R is a substantially hydrocarbyl group containing from 1 to 50 carbon atoms and X is selected from sulfur or oxygen.

2. An organo molybdenum complex according to claim 1 wherein R is an alkyl group containing from about 12 to 28 carbon atoms and X is oxygen.

3. A hydrocarbon-soluble organo molybdenum complex obtained as the reaction product of a hydrocarbyl substituted hydroxy alkylated amine with about one molar equivalent of a molybdenum source of the class consisting of molybdic trioxide, ammonium thiomolybdate, ammonium bismolybdate, molybdenum halides, and ammonium heptamolybdate tetrahydrate.

4. A complex according to claim 3 wherein said amine is N,N',N'-tris(2-hydroxy ethyl)-n-tallow-1,3-diaminopropane and said molybdenum compound is ammonium heptamolybdate tetrahydrate.

5. A hydrocarbon composition comprising a major portion of a hydrocarbon and at least a friction reducing amount of the combination of: (a) an organo molybdenum complex represented by the formula

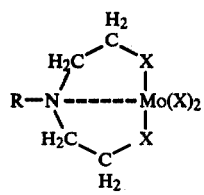

wherein R is a substantially hydrocarbyl group containing from 1 to 50 carbon atoms and X is selected from sulfur or oxygen; and (b) an oil-soluble active sulfur donor, said combination providing from about 0.005 to 0.2 weight percent molybdenum and said sulfur donor being present in at least 0.25 weight percent, all of said weight percent being based on the total weight of said composition.

6. A hydrocarbon composition according to claim 5 wherein said hydrocarbon is mineral oil, said organo complex is an oil-soluble reaction product of a hydrocarbyl substituted hydroxy alkylated amine with about one molar equivalent of a molybdenum source of the class consisting of molybdic trioxide, ammonium thiomolybdate, ammonium bismolybdate, molybdenum halides, and ammonium heptamolybdate tetrahydrate, and said sulfur donor is an oil-soluble dihydrocarbyl ester of dithiophosphoric acid.

7. A hydrocarbon composition according to claim 6 wherein said mineral oil has a viscosity as measured by ASTM D-445 of from about 2 to 40 centistokes at 99° C., said amine is N,N',N'-tris(2-hydroxy ethyl)-n-tallow-1,3-diaminopropane, and said molybdenum compound is ammonium heptamolybdate tetrahydrate, and said active sulfur donor is zinc dihydrocarbyl dithiophosphate present in an amount of from 0.2 to 2 parts by weight per part by weight of said molybdenum complex.

8. A concentrate consisting essentially of from 5 to 80 weight percent of the combination of a hydrocarbon soluble organo molybdenum complex obtained as the reaction product of a hydrocarbyl substituted hydroxy alkylated amine with about one molar equivalent of a molybdenum source of the class consisting of molybdic trioxide, ammonium thiomolybdate, ammonium bismolybdate, molybdenum halides, and ammonium heptamolybdate tetrahydrate and from about 0.1 to 10 parts by weight of active sulfur donor per part by weight of said complex and 20 to 95 weight percent of a solvent for said combination.

9. A gasoline having improved antiwear properties containing from 10 to 1,000 parts per million of an organo molybdenum complex represented by the formula

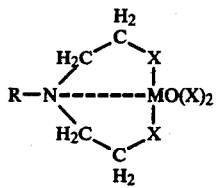

wherein R is a substantially hydrocarbyl group containing from 1 to 50 carbon atoms and X is selected from sulfur or oxygen.

* * * * *